US011426082B2

(12) United States Patent
Sakai et al.

(10) Patent No.: US 11,426,082 B2
(45) Date of Patent: Aug. 30, 2022

(54) PHYSIOLOGICAL INFORMATION PROCESSING APPARATUS AND PHYSIOLOGICAL INFORMATION PROCESSING METHOD

(71) Applicant: NIHON KOHDEN CORPORATION, Tokyo (JP)

(72) Inventors: Mami Sakai, Tokorozawa (JP); Yoshihiro Sugo, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 331 days.

(21) Appl. No.: 16/356,593

(22) Filed: Mar. 18, 2019

(65) Prior Publication Data

US 2019/0298180 A1    Oct. 3, 2019

(30) Foreign Application Priority Data

Mar. 28, 2018    (JP) .............................. JP2018-062700

(51) Int. Cl.
*A61B 5/02*    (2006.01)
*A61B 5/00*    (2006.01)
(Continued)

(52) U.S. Cl.
CPC ........ *A61B 5/02028* (2013.01); *A61B 5/0022* (2013.01); *A61B 5/02007* (2013.01);
(Continued)

(58) Field of Classification Search
CPC .............. A61B 5/02028; A61B 5/0022; A61B 5/02007; A61B 5/02108; A61B 5/02125; A61B 5/0245; A61B 5/029
See application file for complete search history.

(56) References Cited

U.S. PATENT DOCUMENTS

2005/0222514 A1    10/2005  Sugo et al.
2010/0268101 A1    10/2010  Sugo
(Continued)

FOREIGN PATENT DOCUMENTS

EP    2 241 251 A1    10/2010
JP    2010-246801 A   11/2010
(Continued)

OTHER PUBLICATIONS

Extended European Search Report issued in European Patent Application No. 19 16 5191 dated Jun. 26, 2019.
(Continued)

*Primary Examiner* — Lynsey C Eiseman
*Assistant Examiner* — Jessandra F Hough
(74) *Attorney, Agent, or Firm* — Pearne & Gordon LLP

(57) ABSTRACT

A physiological information processing method includes: acquiring electrocardiogram data of a subject; acquiring pulse wave data of the subject; measuring the heart rate based on the electrocardiogram data; measuring the pulse wave transit time based on the electrocardiogram data and the pulse wave data; calculating a cardiac output based on the pulse wave transit time and heart rate which have been measured; calculating the systemic vascular resistance; and correcting the calculated cardiac output based on the systemic vascular resistance.

19 Claims, 4 Drawing Sheets

(51) Int. Cl.
  *A61B 5/021* (2006.01)
  *A61B 5/0245* (2006.01)
  *A61B 5/029* (2006.01)

(52) U.S. Cl.
  CPC ............ *A61B 5/029* (2013.01); *A61B 5/0245* (2013.01); *A61B 5/02108* (2013.01); *A61B 5/02125* (2013.01)

(56) References Cited

U.S. PATENT DOCUMENTS

| | | | |
|---|---|---|---|
| 2011/0060531 A1* | 3/2011 | Sugo | A61B 5/02255 702/19 |
| 2014/0121544 A1* | 5/2014 | Sugo | A61B 5/029 600/484 |
| 2015/0126820 A1 | 5/2015 | Muhlsteff | |

FOREIGN PATENT DOCUMENTS

| | | |
|---|---|---|
| JP | 2014-087484 A | 5/2014 |
| JP | 2015-519940 A | 7/2015 |
| JP | 5779299 B2 | 9/2015 |

OTHER PUBLICATIONS

Alhashemi, J.A., et al., "Cardiac output monitoring: an integrative perspective", Critical Care, Mar. 22, 2011, retrieved from the internet: https://ccforum.biomedcentral.com/track/pdf/101186/cc9996 [retrieved on Jun. 10, 2019].

Rodig, G., "Continuous cardiac output measurement: pulse contour analysis vs. thermodilution technique in cardiac surgical patients", British Journal of Anaesthesia, vol. 82, Apr. 1, 1999, pp. 525-530.

Japanese Office Action dated Nov. 30, 2021 issued in Japanese Patent Application No. 2018-062700.

* cited by examiner

PHYSIOLOGICAL INFORMATION PROCESSING APPARATUS AND PHYSIOLOGICAL INFORMATION PROCESSING METHOD

CROSS-REFERENCE TO RELATED APPLICATIONS

This application is based on and claims priority under 35 USC 119 from Japanese Patent Application No. 2018-062700 filed on Mar. 28, 2018, the contents of which are incorporated herein by reference.

The disclosure relates to a physiological information processing apparatus and a physiological information processing method. The disclosure further relates to a non-transitory computer readable storage medium on which a program for causing a computer to execute the physiological information processing method is stored.

BACKGROUND

Japanese Patent No. 5779299 discloses a method for non-invasively determining a measured value of the cardiac output of a patient based on measurement results of one or more physiological characteristics of the patient. Particularly, Japanese Patent No. 5779299 discloses a method in which measurement results of physiological characteristics including the heart rate, and systolic and diastolic blood pressures of the patient are acquired, and then a measured value of the cardiac output of the patient is determined.

SUMMARY

Recently, it has been reported that the cardiac output of a patient varies in accordance with a parameter relating to the vascular distensibility such as the systemic vascular resistance (hereinafter, such a parameter is referred to as "vascular distensibility parameter"). Therefore, it is desired to calculate the cardiac output of a patient in consideration of the vascular distensibility parameter of the patient. In the case where the cardiac output of a patient is calculated without considering the vascular distensibility parameter of the patient, there is a possibility that a large discrepancy arises between a measured value of the cardiac output which is invasively measured by a cardiac output sensor, and a calculation value of the cardiac output which is calculated by using the heart rate and pulse wave transit time (hereinafter, referred to as PWTT) of the patient. When attention is focused on the phenomenon that the cardiac output varies in accordance with the vascular distensibility parameter (i.e., dependence on the vascular distensibility parameter), consequently, there is room for further improvement of the calculation accuracy of the cardiac output.

The disclosure provides a physiological information processing method and apparatus which can further improve the calculation accuracy of the cardiac output of a patient. The disclosure provides a non-transitory computer readable storage medium on which a program for causing a computer to execute the physiological information processing method is stored.

A physiological information processing method of one mode of the disclosure is to be executed by a computer, and includes:
  acquiring electrocardiogram data of a subject;
  acquiring pulse wave data of the subject;
  measuring a heart rate based on the electrocardiogram data;
  measuring a pulse wave transit time based on the electrocardiogram data and the pulse wave data;
  calculating a cardiac output based on the pulse wave transit time and heart rate which have been measured;
  calculating a vascular distensibility parameter relating to a vascular distensibility; and
  correcting the calculated cardiac output based on the vascular distensibility parameter.

Moreover, a non-transitory computer readable storage medium on which a program for causing a computer to execute the physiological information processing method is stored are provided.

A physiological information processing apparatus of one mode of the disclosure includes:
  one or more processor; and
  one or more memory which stores computer readable instructions.

When the computer readable instructions are executed by the processor, the physiological information processing apparatus
  acquires electrocardiogram data of a subject,
  acquires pulse wave data of the subject,
  measures a heart rate based on the electrocardiogram data,
  measures a pulse wave transit time based on the electrocardiogram data and the pulse wave data,
  calculates a cardiac output based on the pulse wave transit time and heart rate which have been measured,
  calculates a vascular distensibility parameter relating to a vascular distensibility, and
  corrects the calculated cardiac output based on the vascular distensibility parameter.

According to the disclosure, it is possible to provide a physiological information processing method and apparatus which can further improve the calculation accuracy of the cardiac output of a patient. Moreover, it is possible to provide a non-transitory computer readable storage medium on which a program for causing a computer to execute the physiological information processing method is stored.

DESCRIPTION OF EMBODIMENTS

Hereinafter, an embodiment will be described with reference to the drawings. Initially, the hardware configuration of a physiological information processing apparatus 1 of an embodiment of the presently disclosed subject matter (hereinafter, referred to simply as the embodiment) will be described.

Figure 1:
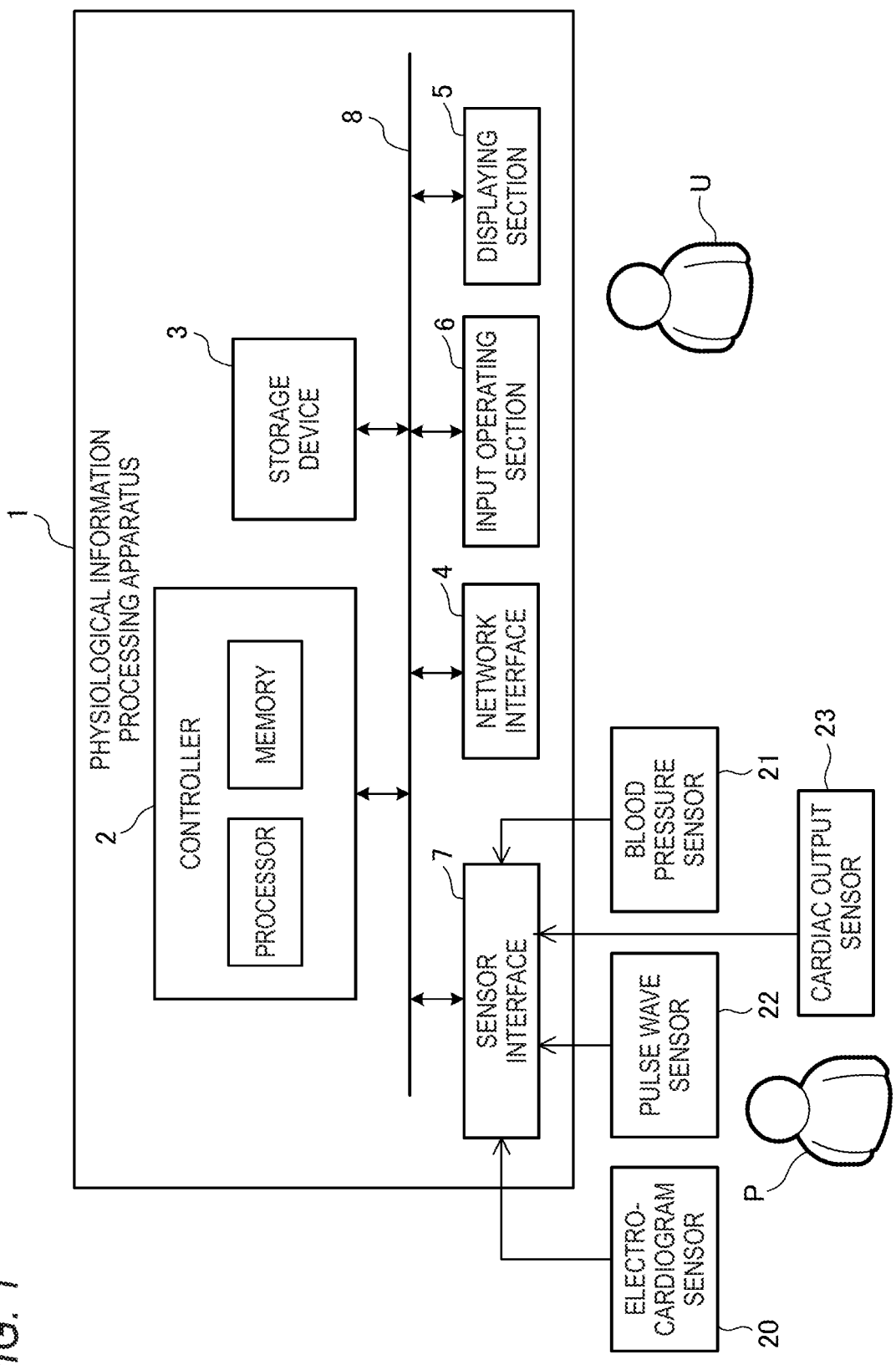
FIG. 1 illustrates an example of a hardware configuration of a physiological information processing apparatus of an embodiment of the presently disclosed subject matter.

FIG. 1 illustrates an example of the hardware configuration of the physiological information processing apparatus 1 of the embodiment. As illustrated in FIG. 1, the physiological information processing apparatus 1 (hereinafter, referred to simply as the processing apparatus 1) includes a controller 2, a storage device 3, a network interface 4, a displaying section 5, an input operating section 6, and a sensor interface 7. These components are communicably connected to one another via a bus 8.

The processing apparatus 1 may be an apparatus (a patient monitor or the like) dedicated to display of a trend graph of vital signs of a subject P, or, for example, a personal computer, a workstation, a smart phone, a tablet, or a wearable device (such as a smart watch or an AR glass) which is to be attached to the body (such as the arm or the head) of a medical person U.

The controller 2 includes a memory and a processor. The memory is configured so as to store computer readable instructions (programs), and may be configured by, for example, a ROM (Read Only Memory) which stores various programs and the like, and a RAM (Random Access Memory) having a plurality of work areas in which various programs to be executed by the processor, and the like are stored. Alternatively, the memory may be configured by a flash memory or the like. For example, the processor is a CPU (Central Processing Unit), an MPU (Micro Processing Unit), and/or a GPU (Graphics Processing Unit). The CPU may be configured by a plurality of CPU cores. The GPU may be configured by a plurality of GPU cores. The processor may be configured so as to develop a designated one of the various programs installed in the storage device 3 or the ROM, in the RAM, and execute various processes in cooperation with the RAM.

The processor may develop a physiological information processing program which will be described later, in the RAM, and execute the program in cooperation with the RAM, thereby enabling the controller 2 to control various operations of the processing apparatus 1. The physiological information processing program will be described in detail later.

For example, the storage device 3 is a storage device such as an HDD (Hard Disk Drive), an SSD (Solid State Drive), or a flash memory, and configured so as to store programs and various data. The physiological information processing program may be incorporated in the storage device 3. The storage device 3 may store physiological information data such as electrocardiogram data, blood pressure data, and pulse wave data of the subject P. For example, electrocardiogram data which are acquired by an electrocardiogram sensor 20 may be stored in the storage device 3 through the sensor interface 7.

The network interface 4 is configured so as to connect the processing apparatus 1 to a communication network. Specifically, the network interface 4 may include various wired connection terminals for communicating with an external apparatus such as a server through the communication network. The network interface 4 may further include various processing circuits, antenna, and the like for wirelessly communicating with an access point. For example, the standard of wireless communication between the access point and the processing apparatus 1 is the Wi-Fi (registered trademark), the Bluetooth (registered trademark), the ZigBee (registered trademark), the LPWA, or a fifth generation mobile communication system (5G). The communication network is a LAN (Local Area Network), a WAN (Wide Area Network), the Internet, or the like. For example, the physiological information processing program and physiological information data may be acquired from the server placed in the communication network through the network interface 4.

The displaying section 5 may be a display device such as a liquid crystal display or an organic EL display, or that such as a transmission or non-transmission head mounted display which is to be attached to the head of the operator. Alternatively, the displaying section 5 may be a projector device which projects an image onto a screen.

The input operating section 6 is configured so as to receive an input operation performed by the medical person U who operates the processing apparatus 1, and produce an instruction signal corresponding to the input operation. For example, the input operating section 6 is configured by a touch panel which is placed overlappingly on the displaying section 5, operation buttons which are attached to the housing, or a mouse and/or a keyboard. The instruction signal which is produced by the input operating section 6 is transmitted to the controller 2 via the bus 8, and then the controller 2 executes a predetermined operation according to the instruction signal.

The sensor interface 7 is an interface which enables vital sensors such as the electrocardiogram sensor 20, a blood pressure sensor 21, and a pulse wave sensor 22 to be communicably connected to the processing apparatus 1. The sensor interface 7 may include input terminals to which the physiological data output from these vital sensors are input. The input terminals may be physically connected to connectors of the vital sensors. The sensor interface 7 may further include various processing circuits, antenna, and the like for wirelessly communicating with the vital sensors.

The electrocardiogram sensor 20 is configured so as to acquire electrocardiogram data indicating the electrocardiogram waveform of the subject P. The pulse wave sensor 22 is configured so as to acquire pulse wave data indicating the pulse wave of the subject P. The blood pressure sensor 21 is configured so as to acquire blood pressure data indicating a temporal change of the blood pressure (particularly, the arterial blood pressure and/or the venous blood pressure) of the subject P. The blood pressure sensor 21 may be configured by a plurality of blood pressure sensors. The blood pressure sensor 21 may invasively acquire the blood pressure data of the subject P, or non-invasively acquire the blood pressure data of the subject P. A cardiac output sensor 23 is configured so as to acquire cardiac output data indicating a temporal change of the cardiac output of the subject P.

Figure 2:
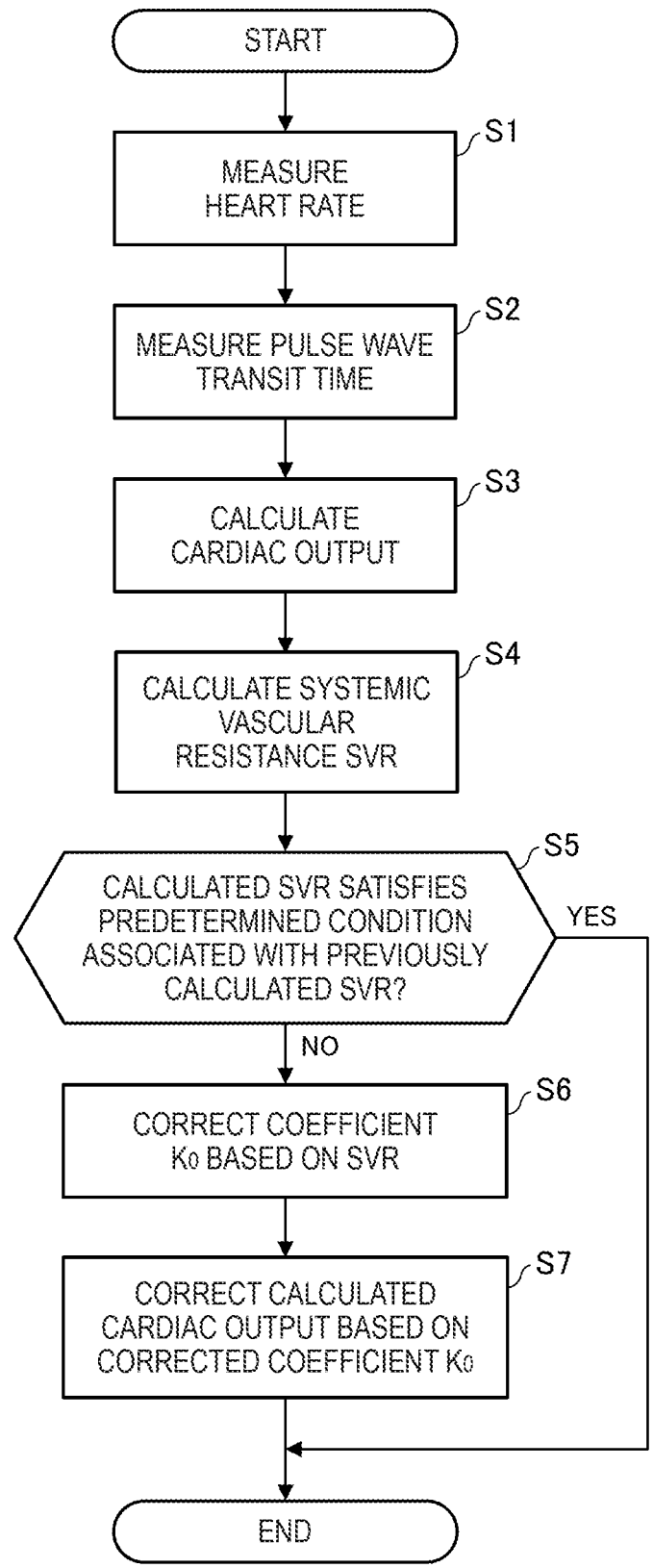
FIG. 2 is a flowchart for explaining an example of a physiological information processing method of the embodiment of the presently disclosed subject matter.

Next, a physiological information processing method of the embodiment will be described with reference to FIG. 2. FIG. 2 is a flowchart illustrating an example of the physiological information processing method of the embodiment. As illustrated in FIG. 2, the controller 2 firstly acquires the electrocardiogram data from the electrocardiogram sensor 20, and the pulse wave data from the pulse wave sensor 22. Next, the controller 2 measures the heart rate of the subject P based on the acquired electrocardiogram data (step S1). Specifically, the controller 2 specifies a plurality of RR intervals indicating the time intervals between adjacent R waves during a predetermined time period, from the electrocardiogram data. Then, the controller 2 calculates the mean RR interval indicating the mean value of the plurality of RR intervals during the predetermined time period, and thereafter measures the heart rate (bpm) of the subject P from the mean RR interval based on the relational expression of "heart rate=60/mean RR interval." The controller 2 may calculate the heart rate every predetermined time interval (for example, every one second).

Next, the controller 2 measures in step S2 the pulse wave transit time (hereinafter, referred to as PWTT) based on the electrocardiogram data and the pulse wave data. The PWTT means a time interval from the peak point of a predetermined R wave of an electrocardiogram to the rising point of a predetermined pulse waveform which appears next to the predetermined R wave. Therefore, the controller 2 specifies the time of the peak point of the predetermined R wave from the electrocardiogram data, and further specifies that of the rising point of the predetermined pulse waveform which appears next to the predetermined R wave, from the pulse wave data. Next, the controller 2 calculates the time interval between the time of the rising point of the predetermined pulse waveform and that of the peak point of the predetermined R wave, thereby measuring the PWTT. The controller 2 may calculate the PWTT every predetermined time interval (for example, every one second).

Next, the controller 2 calculates the cardiac output of the subject P based on the PWTT and heart rate which have been measured (step S3). Specifically, the controller 2 calculates the cardiac output from the PWTT and the heart rate in accordance with following relational expression (1). In the expression, esCCO (estimated Continuous Cardiac Output) indicates a calculated cardiac output, HR indicates the heart rate, and $K_0$, $\alpha$, and $\beta$ are specific coefficients which are set for each subject. Specific examples of methods for deriving the coefficients $K_0$, $\alpha$, and $\beta$ are described in, for example, Japanese Patent No. 4,742,644 that is incorporated by reference herein. The controller 2 may calculate the cardiac output every predetermined time interval (for example, every one second).

$$\text{esCCO} = K_0 \times (\alpha \times \text{PWTT} + \beta) \times \text{HR} \quad (1)$$

Next, the controller 2 calculates in step S4 the systemic vascular resistance (hereinafter, referred to as SVR) of the subject P. The SVR is an example of the vascular distensibility parameter relating to the vascular distensibility of the subject P. Specifically, the controller 2 acquires blood pressure data indicating a temporal change of the arterial blood pressure from the blood pressure sensor 21, and then calculates the mean blood pressure (MAP) of the subject P from the acquired blood pressure data. Moreover, the controller 2 acquires blood pressure data indicating a temporal change of the central venous pressure (CVP) from the blood pressure sensor 21. Furthermore, the controller 2 acquires cardiac output data indicating a temporal change of the cardiac output from the cardiac output sensor 23, and then calculates the cardiac output CO. Thereafter, the controller 2 calculates the SVR from the mean blood pressure (MAP), the central venous pressure (CVP), and the cardiac output (CO) in accordance with following relational expression (2):

$$\text{SVR} = \{(\text{MAP} - \text{CVP}) \times 80\} / \text{CO} \quad (2)$$

Further, the controller 2 may calculate the SVR every predetermined time interval (for example, every one second).

Next, the controller 2 determines in step S5 whether the newly calculated SVR satisfies a predetermined condition associated with the previously calculated SVR or not. The previously calculated SVR may be the $\text{SVR}_{n-1}$ (n is an integer of 2 or more) which is calculated just before the newly calculated $\text{SVR}_n$, the initially calculated SVR (i.e., $\text{SVR}_1$), or an $\text{SVR}_m$ (m is an integer that is smaller than n) which is calculated before a predetermined time period.

Examples of "predetermined condition associated with the previously calculated SVR" are the following three conditions:

1) condition associated with a variation $\Delta \text{SVR}$ between the newly calculated SVR and the previously calculated SVR;

2) condition associated with a ratio of the variation $\Delta \text{SVR}$ to the newly calculated SVR or the previously calculated SVR; and 3) condition associated with a predetermined range which is set based on the previously calculated SVR.

The above conditions 1) to 3) will be described in detail below. For the sake of convenience of the description, "previously calculated SVR" is assumed to be the $\text{SVR}_{n-1}$ which is calculated just before.

In the case of condition 1), the controller 2 determines whether the variation $\Delta \text{SVR} = |\text{SVR}_n - \text{SVR}_{n-1}|$ between the newly calculated $\text{SVR}_n$ and the just before calculated $\text{SVR}_{n-1}$ is equal to or smaller than a predetermined value $\Delta \text{SVR}_{th}$ or not. Here, the predetermined value $\Delta \text{SVR}_{th}$ can be appropriately set on the side of a medical facility. If it is determined that the variation $\Delta \text{SVR}$ is equal to or smaller than the predetermined value $\Delta \text{SVR}_{th}$ (in step S5, YES), the controller 2 ends the process. By contrast, if it is determined that the variation $\Delta \text{SVR}$ is larger than the predetermined value $\Delta \text{SVR}_{th}$ (in step S5, NO), the controller 2 executes the process of step S6.

In the case of condition 2), the controller 2 determines whether the ratio R of the variation $\Delta \text{SVR} = |\text{SVR}_n - \text{SVR}_{n-1}|$ to the newly calculated $\text{SVR}_n$ (or the just before calculated $\text{SVR}_{n-1}$) is equal to or smaller than a predetermined value $R_{th}$ or not. Here, $R = \Delta \text{SVR}/\text{SVR}_n \times 100\%$ or $R = \Delta \text{SVR}/\text{SVR}_{n-1} \times 100\%$. The predetermined value $R_{th}$ can be appropriately set on the side of the medical facility. If it is determined that the ratio R is equal to or smaller than the predetermined value $R_{th}$ (in step S5, YES), the controller 2 ends the process. By contrast, if it is determined that the ratio R is larger than the predetermined value $R_{th}$ (in step S5, NO), the controller 2 executes the process of step S6.

In the case of condition 3), if it is determined that the newly calculated $\text{SVR}_n$ is included within a predetermined range S which is set based on the previously calculated $\text{SVR}_{n-1}$ (in step S5, YES), the controller 2 ends the process. By contrast, if it is determined that the newly calculated $\text{SVR}_n$ is not included within the predetermined range S which is set based on the previously calculated $\text{SVR}_{n-1}$ (in step S5, NO), the controller 2 executes the process of step S6. Here, the predetermined range S may be set as $\text{SVR}_{n-1} \pm \gamma$ ($\gamma$ is a predetermined value). If it is determined that the $\text{SVR}_n$ is $\text{SVR}_{n-1} - \gamma \leq \text{SVR}_n \leq \text{SVR}_{n-1} + \gamma$ (in step S5, YES), the controller 2 ends the process. By contrast, if it is determined that the $\text{SVR}_n$ is not $\text{SVR}_{n-1} - \gamma \leq \text{SVR}_n \leq \text{SVR}_{n-1} + \gamma$ (in step S5, NO), the controller 2 executes the process of step S6.

As described above, in the case where the newly calculated $\text{SVR}_n$ largely varies from the just before calculated $\text{SVR}_{n-1}$, the determination result of step S5 is NO, and, in the case where the newly calculated $\text{SVR}_n$ does not largely vary from the just before calculated $\text{SVR}_{n-1}$, the determination result of step S5 is YES. In this way, in the case where the predetermined condition is satisfied in step S5 (in other words, in the case where the $\text{SVR}_n$ does not largely vary from the $\text{SVR}_{n-1}$), the processes of steps S6 and S7 are not executed, and therefore the computing load of the controller 2 (processor) can be reduced.

Next, the controller 2 corrects in step S6 the coefficient $K_0$ which is used in relational expression (1), based on the newly calculated $\text{SVR}_n$. For example, the controller 2 can calculate the corrected coefficient $K_0$ from the $\text{SVR}_n$, based on following relational expression (3):

$$\text{corrected coefficient } K_0 = K_0 + \Delta K_n = K_0 + c \times \text{SVR}_n + d \quad (3)$$

Here, the slope c and the intercept d are values which are determined by linearly approximating the correlation between $\Delta K_i = K_i - K_0$ (i is an integer of 1 or more) and the $SVR_i$, respectively. Namely, the correlation between $\Delta K_i$ and the $SVR_i$ can be expressed as a linear function ($\Delta K_i = c \times SVR_i + d$) based on a plurality of $\Delta K_i$ and a plurality of $SVR_i$ each of which is associated with corresponding one of the plurality of $\Delta K_i$. In this way, the slope c and the intercept d can be determined. The values of the slope c and the intercept d may be appropriately set on the side of the medical facility.

Next, the controller 2 again calculates in step S7 the cardiac output based on the corrected coefficient $K_0$, thereby correcting the cardiac output (esCCO) which is calculated in step S3. Specifically, the controller 2 again calculates the cardiac output based on following relational expression (4):

$$\text{corrected } esCCO = \text{corrected coefficient } K_0 \times (\alpha \times PWTT + \beta) \times HR \quad (4)$$
$$= (K_0 + c \times SVRn + d) \times (\alpha \times PWTT + \beta) \times HR$$

According to the embodiment, as described above, the coefficient $K_0$ is corrected based on the newly calculated $SVR_n$, and then the cardiac output is again calculated based on the corrected coefficient $K_0$. Since the calculated cardiac output is corrected in consideration of the SVR which is an example of the vascular distensibility parameter as described above, it is possible to provide the processing apparatus 1 in which the calculation accuracy of the cardiac output of the subject can be further improved.

The processes (particularly, the processes illustrated in steps S3 to S7) illustrated in FIG. 2 may be repeatedly performed every predetermined time interval (for example, every one second). For example, the controller 2 acquires an (n+1)-th $esCCO_{n+1}$ or corrected $esCCO_{n+1}$ after an elapse of a predetermined time period from acquisition of an n-th $esCCO_n$ or corrected $esCCO_n$. The sequence of the processes illustrated in FIG. 2 is not particularly limited. For example, the process of step S1 may be performed after that of step S2. Moreover, the process of step S4 may be performed before that of step S1.

(Modification of the Embodiment)

Figure 3:
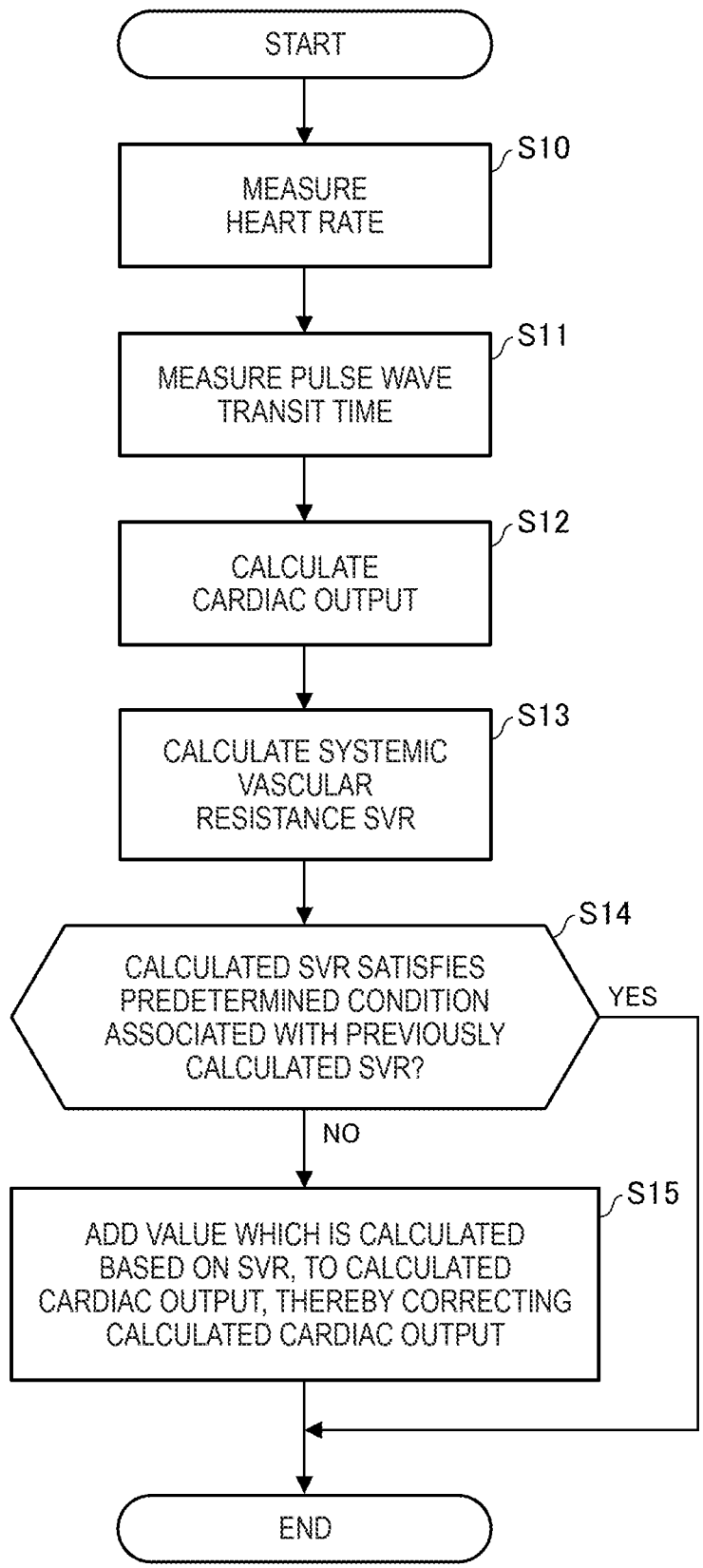
FIG. 3 is a flowchart for explaining an example of a physiological information processing method of a modification of the embodiment of the presently disclosed subject matter.

Next, a physiological information processing method of a modification of the embodiment (hereinafter, referred to merely as modification) will be described with reference to FIG. 3. FIG. 3 is a flowchart illustrating an example of the physiological information processing method of the modification. The physiological information processing method of the modification is different from that of the embodiment in the method for correcting the calculated value of the cardiac output. Therefore, the processes of steps S10 to S14 illustrated in FIG. 3 are identical with those of steps S1 to S5 illustrated in FIG. 2, and hence only the process of step S15 will be described below.

As illustrated in FIG. 3, in step S15, the controller 2 adds a value which is calculated based on the newly calculated $SVR_n$, to the cardiac output that is calculated in step S12, thereby correcting the cardiac output that is calculated in step S12. Specifically, the controller 2 corrects the cardiac output based on following relational expression (5).

$$\text{corrected } esCCO = K_0 \times (\alpha \times PWTT + \beta) \times HR + \Delta esCCO \quad (5)$$
$$= K_0 \times (\alpha \times PWTT + \beta) \times HR + e \times SVR_n + f$$

Here, the slope e and the intercept f are values which are determined by linearly approximating the correlation between $\Delta esCCO_i = esCCO_i - esCCO_0$ (i is an integer of 1 or more) and the $SVR_i$, respectively, and $esCCO_0$ is a predetermined cardiac output which is determined in the case of $PWTT = PWTT_0$ and $HR = HR_0$. For example, $PWTT_0$ is the value of the PWTT in the stable condition of the subject, and $HR_0$ is the value of HR in the stable condition of the subject.

Namely, the correlation between the $\Delta esCCO_i$ and the $SVR_i$ can be expressed as a linear function ($\Delta esCCO_i = e \times SVR_i + f$) based on a plurality of $\Delta esCCO_i$ and a plurality of $SVR_i$ each of which is associated with corresponding one of the plurality of $\Delta esCCO_i$. In this way, the slope e and the intercept f can be determined. The values of the slope e and the intercept f may be appropriately set on the side of the medical facility.

According to the modification, as described above, the calculated value of the cardiac output is corrected by adding the value of $\Delta esCCO = e \times SVR_n + f$ which is calculated based on the newly calculated $SVR_n$, to the cardiac output which is calculated in step S12. Since the calculated value of the cardiac output is corrected in consideration of the SVR which is an example of the vascular distensibility parameter as described above, it is possible to provide the processing apparatus 1 in which the calculation accuracy of the cardiac output of the subject can be further improved.

Figure 4A:
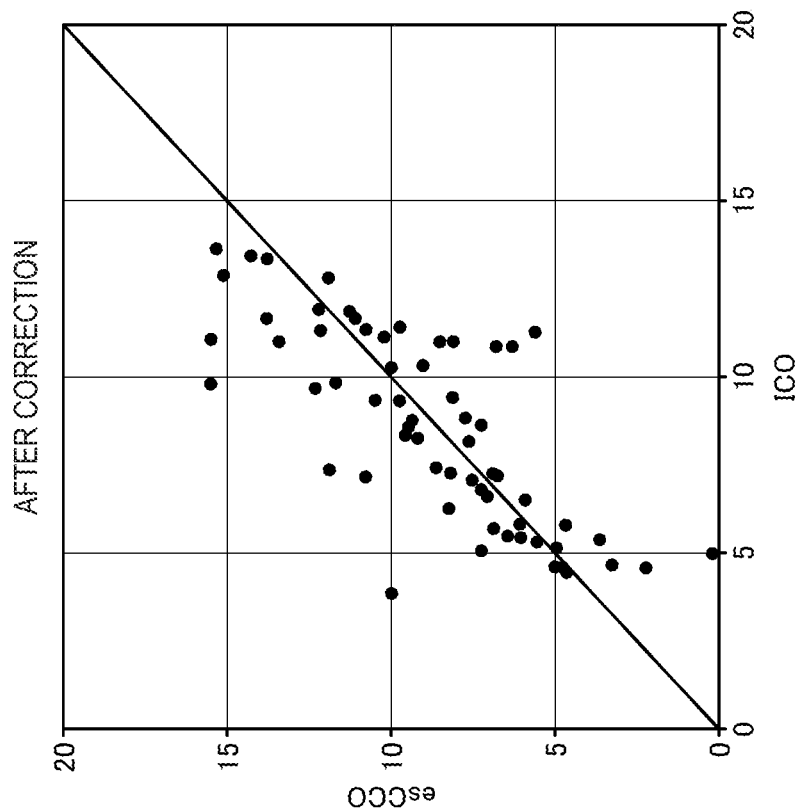
FIG. 4A illustrates relationships between a calculated value of the cardiac output before correction and a measured value of the cardiac output.
Figure 4B:
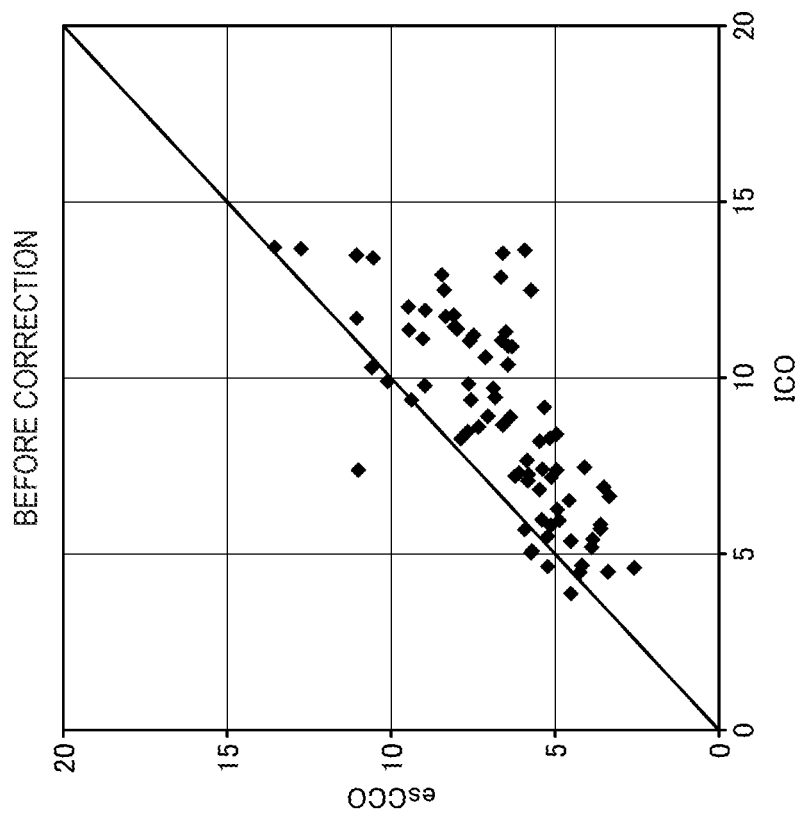
FIG. 4B illustrates relationships between a calculated value of the cardiac output after correction and the measured value of the cardiac output.

In this respect, the degree by which the calculation accuracy of the cardiac output is improved will be described with reference to FIGS. 4A and 4B. FIG. 4A is a view illustrating relationships between the calculated value esCCO (the ordinate) of the cardiac output before correction, and a measured value ICO (the abscissa) of the cardiac output, and FIG. 4B is a view illustrating relationships between the calculated value esCCO (the ordinate) of the cardiac output after correction, and the measured value ICO (the abscissa) of the cardiac output. Here, the calculated value esCCO of the cardiac output before correction which is illustrated in FIG. 4A corresponds to the cardiac output that is calculated in step S12 of FIG. 3. By contrast, the calculated value of the cardiac output after correction which is illustrated in FIG. 4B corresponds to the cardiac output that is corrected in step S15 of FIG. 3. In the case where the accuracy of a calculated value of the cardiac output is high, it is contemplated that a plurality of plots each of which is configured by calculated and measured values of the cardiac output are located on or in the vicinity of a linear line expressed by esCCO=ICO. Form this point of view, when the plots illustrated in FIG. 4A are compared with those illustrated in FIG. 4B, it is known that the plots illustrated in FIG. 4B are nearer to the linear line showing esCCO=ICO than those illustrated in FIG. 4A. Therefore, it is understood that the accuracy of a calculated value of the cardiac output is improved by correcting the calculated value of the cardiac output based on the SVR.

The processes (particularly, the processes illustrated in steps S12 to S15) illustrated in FIG. 3 may be repeatedly performed every predetermined time interval (for example, every one second). For example, the controller 2 acquires an (n+1)-th $esCCO_{n+1}$ or corrected $esCCO_{n+1}$ after an elapse of a predetermined time period from acquisition of an n-th $esCCO_n$ or corrected $esCCO_n$.

Although, in the descriptions of the embodiment and the modification, the SVR is used as an example of the vascular distensibility parameter, the vascular distensibility parameter is not limited to the SVR. In place of the SVR, for example, the arterial elastic modulus, the dynamic arterial elastic modulus, or the pulse-amplitude index may be used as an example of the vascular distensibility parameter. Also in this case, samely or similarly, the calculated value of the cardiac output is corrected in consideration of the arterial elastic modulus, the dynamic arterial elastic modulus, or the pulsation rate, and therefore it is possible to provide the processing apparatus 1 in which the calculation accuracy of the cardiac output of the subject can be further improved.

In order to realize the processing apparatus 1 of the embodiment by using software, the physiological information processing program may be pre-installed in the storage device 3 or the ROM. Alternatively, the physiological information processing program may be stored on a computer readable storage medium such as a magnetic disk (such as an HDD or a floppy disk), an optical disk (such as a CD-ROM, a DVD-ROM, or a Blu-ray (registered trademark) disk), a magneto-optical disk (such as an MO), or a flash memory (such as an SD card, a USB memory, or an SSD). In the alternative, when the physiological information processing program which is stored in the storage medium may be installed in the storage device 3. Then, the program which is installed in the storage device 3 is loaded into the RAM, and thereafter the processor executes the program which is loaded into the RAM. In this way, the physiological information processing method of the embodiment is executed by the processing apparatus 1.

The physiological information processing program may be downloaded from a computer on a communication network, through the network interface 4. The downloaded program may be installed in the storage device 3.

Although the embodiment of the presently disclosed subject matter has been described, the technical scope of the presently disclosed subject matter should not be limitedly interpreted by the description of the embodiment. It should be understood by those skilled in the art that the embodiment is a mere example, and may be variously changed within the scope of the presently disclosed subject matter as defined in the claims. The technical scope of the presently disclosed subject matter should be determined based on the scope of the presently disclosed subject matter as defined in the claims, and the scope of equivalence thereof.

What is claimed is:

1. A physiological information processing method that is executed by a computer, the method comprising:
   acquiring electrocardiogram data of a subject;
   acquiring pulse wave data of the subject;
   measuring a heart rate based on the electrocardiogram data;
   measuring a pulse wave transit time based on the electrocardiogram data and the pulse wave data;
   calculating a cardiac output by using the measured pulse wave transit time, the measured heart rate, and a coefficient parameter;
   calculating a vascular distensibility parameter relating to a vascular distensibility;
   calculating a corrected coefficient parameter by linearly approximating a correlation between a change in the coefficient parameter and the vascular distensibility parameter; and
   correcting the calculated cardiac output by using the corrected coefficient parameter.

2. The physiological information processing method according to claim 1, wherein when the calculated vascular distensibility parameter does not satisfy a predetermined condition associated with a previously calculated vascular distensibility parameter, the correcting of the calculated cardiac output is performed.

3. The physiological information processing method according to claim 2, wherein the predetermined condition is associated with a variation between the calculated vascular distensibility parameter and the previously calculated vascular distensibility parameter.

4. The physiological information processing method according to claim 2, wherein the predetermined condition is associated with a ratio of the variation between the calculated vascular distensibility parameter and the previously calculated vascular distensibility parameter, to the calculated vascular distensibility parameter or the previously calculated vascular distensibility parameter.

5. The physiological information processing method according to claim 2, wherein the predetermined condition is associated with a predetermined range which is set based on the previously calculated vascular distensibility parameter.

6. The physiological information processing method according to claim 2, wherein the previously calculated vascular distensibility parameter is a just before calculated vascular distensibility parameter, an initially calculated vascular distensibility parameter, or a vascular distensibility parameter which is calculated before a predetermined time period.

7. The physiological information processing method according to claim 1, wherein the vascular distensibility parameter is a systemic vascular resistance, an arterial elastic modulus, a dynamic arterial elastic modulus, or a pulse-amplitude index.

8. The physiological information processing method according to claim 1, wherein the cardiac output is calculated by a following expression:

$$esCCO = K_0 \times (\alpha \times PWTT + \beta) \times HR \quad (1)$$

where esCCO is the cardiac output, PWTT is the pulse wave transit time, HR is the heart rate, $K_0$ is the coefficient parameter, and $\alpha$ and $\beta$ are arbitrary values.

9. The physiological information processing method according to claim 1,
   wherein, the cardiac output is calculated by a following expression:

$$esCCO = K_0 \times (\alpha \times PWTT + \beta) \times HR$$

where esCCO is the cardiac output, PWTT is the pulse wave transit time, HR is the heart rate, $K_0$ is the coefficient parameter, and $\alpha$ and $\beta$ are arbitrary values, and
   wherein correcting the calculated cardiac output includes:
      adding a value which is calculated based on the vascular distensibility parameter, to the calculated cardiac output, thereby correcting the calculated cardiac output.

10. A non-transitory computer readable storage medium on which a program for causing a computer to execute the physiological information processing method according to claim 1 is stored.

11. A physiological information processing apparatus comprising:
   one or more processor; and
   one or more memory which stores computer readable instructions,
   wherein when the computer readable instructions are executed by the processor, the physiological information processing apparatus configured to:
      acquire electrocardiogram data of a subject,
      acquire pulse wave data of the subject, measure a heart rate based on the electrocardiogram data, measure a pulse wave transit time based on the electrocardiogram data and the pulse wave data, calculate a cardiac output by using the measured pulse wave transit time, the measured heart rate, and a coefficient parameter, calculate a vascular distensibility parameter relating to a vascular distensibility, calculate a corrected coefficient parameter by linearly approximating a correlation between a change in the coefficient parameter and the vascular distensibility parameter, and correct the calculated cardiac output by using the corrected coefficient parameter.

12. The physiological information processing apparatus according to claim 11, wherein in a case where the calculated vascular distensibility parameter does not satisfy a predetermined condition associated with a previously calculated vascular distensibility parameter, the physiological information processing apparatus corrects the calculated cardiac output based on the vascular distensibility parameter.

13. The physiological information processing apparatus according to claim 12, wherein the predetermined condition is associated with a variation between the calculated vascular distensibility parameter and the previously calculated vascular distensibility parameter.

14. The physiological information processing apparatus according to claim 12, wherein the predetermined condition is associated with a ratio of the variation between the calculated vascular distensibility parameter and the previously calculated vascular distensibility parameter, to the calculated vascular distensibility parameter or the previously calculated vascular distensibility parameter.

15. The physiological information processing apparatus according to claim 12, wherein the predetermined condition is associated with a predetermined range which is set based on the previously calculated vascular distensibility parameter.

16. The physiological information processing apparatus according to claim 11, wherein the previously calculated vascular distensibility parameter is a just before calculated vascular distensibility parameter, an initially calculated vascular distensibility parameter, or a vascular distensibility parameter which is calculated before a predetermined time period.

17. The physiological information processing apparatus according to claim 11, wherein the vascular distensibility parameter is a systemic vascular resistance, an arterial elastic modulus, a dynamic arterial elastic modulus, or pulse-amplitude index.

18. The physiological information processing apparatus according to claim 11, wherein the physiological information processing apparatus is configured to calculate the cardiac output by a following expression:

$$esCCO = K_0 \times (\alpha \times PWTT + \beta) \times HR$$

where esCCO is the cardiac output, PWTT is the pulse wave transit time, HR is the heart rate, $K_0$ is the coefficient parameter, and $\alpha$ and $\beta$ are arbitrary values.

19. The physiological information processing apparatus according to claim 11, wherein the physiological information processing apparatus is configured to calculate the cardiac output by a following expression:

$$esCCO = K_0 \times (\alpha \times PWTT + \beta) \times HR$$

where esCCO is the cardiac output, PWTT is the pulse wave transit time, HR is the heart rate, $K_0$ is the coefficient parameter, and $\alpha$ and $\beta$ are arbitrary values, and wherein the physiological information processing apparatus is configured to add a value which is calculated based on the vascular distensibility parameter, to the calculated cardiac output, thereby correcting the calculated cardiac output.

* * * * *